United States Patent [19]

Chao et al.

[11] Patent Number: 4,855,930

[45] Date of Patent: Aug. 8, 1989

[54] METHOD AND APPARTATUS FOR IMPROVED TIME-RESOLVED FLUORESCENCE SPECTROSCOPY

[75] Inventors: Yong-Sheng Chao, Glaston; Salvador M. Fernandez, Hartford; Ernest F. Guignon, Canton, all of Conn.

[73] Assignee: Chimerix Corporation, Glastonbury, Conn.

[21] Appl. No.: 31,288

[22] Filed: Mar. 27, 1987

[51] Int. Cl.$^4$ .......................... G01J 1/58; G06F 15/20
[52] U.S. Cl. .................................. 364/497; 250/458.1; 356/318; 364/554
[58] Field of Search ............ 250/361 C, 458.1, 459.1; 356/300, 308, 318, 319, 346; 364/497, 498, 550, 554; 378/44, 45

[56] References Cited

U.S. PATENT DOCUMENTS

| | | | |
|---|---|---|---|
| 4,035,080 | 7/1977 | Yamaguchi | 356/346 X |
| 4,058,732 | 11/1977 | Wieder | 250/461 B |
| 4,198,567 | 4/1980 | Eneroth et al. | 250/459.1 |
| 4,231,750 | 11/1980 | Dowben et al. | 23/230 B |
| 4,330,207 | 5/1982 | Nogami et al. | 364/498 X |
| 4,368,047 | 1/1983 | Andrade et al. | 435/4 |
| 4,385,126 | 5/1983 | Chen et al. | 436/518 |
| 4,511,986 | 4/1985 | Bellar et al. | 356/346 X |
| 4,582,809 | 4/1986 | Block et al. | 436/527 |
| 4,641,032 | 2/1987 | Mauchien et al. | 356/318 X |
| 4,652,755 | 3/1987 | Solomon et al. | 356/346 X |

FOREIGN PATENT DOCUMENTS 62-28844 2/1986 Japan.
2129548A 5/1984 United Kingdom.
WO86/02734 5/1986 World Int. Prop. O..

OTHER PUBLICATIONS

G. T. Longerbeam et al.: "High Speed Single Transient Oscilloscopes, the State of the Art, and Current Potential for Mating to On-Line Computers", pp. 13/4:1-10 w/ 1969 Wescon Technical Papers, Part 4, Instruments and Systems, Western Electronic Show and Convention, 19-22, Aug. 1969 (US).

"Subnanosecond Fluorescence Waveforms Measurements with a Dual Time-Scale Microprocessor-Controlled Averager", Docchio et al., *Rev. Sci. Instrum.*, 52(11), Nov. 1981, pp. 1671-1675.

R. I. Sha'afi et al., "Fast Methods in Physical Biochemistry and Cell Biology", 1983, published by Elsevier, pp. 221-279.

"Applications of Lasers in Analytical Molecular Fluorescence Spectroscopy", *Modern Fluorescence Spectroscopy*, vol. 4, 1981, J. J. Richardson, p. 15.

"A High Sensitivity Television Camera System for Pico-Second Spectroscopy", pp. 947-948, *Japanese Journal of Applied Physics*, vol. 15, No. 5, 1976, H. Saito et al.

"Time-Resolved Fluorescence Spectroscopy", Salvador M. Fernandez, Fast Methods in Physical Biochemistry and Cell Biology, Elsevier Science Publishers, 1983, pp. 221-280.

*Primary Examiner*—Parshotam S. Lall
*Assistant Examiner*—Edward R. Cosimano
*Attorney, Agent, or Firm*—Hamilton, Brook, Smith & Reynolds

[57] ABSTRACT

A method and apparatus for time-resolved fluorescence spectroscopy is described in which laser light from a single pulse is used to excite fluorescent photons in a sample, which fluorescence is detected by a PMT optimized for linearity and response time to produce photoelectrons which generate a current at the PMT anode. This current is discharged through an R/C network to produce a voltage amplitude waveform which is converted to an optical image, intensified, stored and digitized. The digitized version of the optical image is processed in a data processor to calculate the true fluorescence impulse response.

23 Claims, 2 Drawing Sheets

METHOD AND APPARATUS FOR IMPROVED TIME-RESOLVED FLUORESCENCE SPECTROSCOPY

DESCRIPTION

1. Technical Field

The invention relates to fluorescence spectroscopy and instrumentation and methods employed therein.

2. Background Art

Pulse fluorometry is one of the theoretically possible approaches for performing time-resolved fluorescence measurements. An overview of this field is presented in "Time-Resolved Fluorescence Spectroscopy" by S. M. Fernandez in *Fast Methods in Physical Biochemistry and Cell Biology*, R. I. Sha'afi and S. M. Fernandez (Eds.) Elsevier Science Publishers 1983.

A general technique for studying the dynamic behavior of a physical system is to determine the response of the system to an "instantaneous perturbation"; i.e., its *impulse response*. The impulse response of a fluorescent system to an instantaneous light pulse consists of the intensity of the fluorescence emission as a function of time after the disappearance of the perturbing impulse. For a homogeneous fluorescent system, i.e., one made up of identical fluorescent molecules, the impulse response takes the form of an exponential decay:

$$f(t) = A\exp(-k/t) \quad (1)$$

where f(t) is the intensity of the fluorescence at time t and k is the rate constant for emission, i.e., the reciprocal of the fluorescence lifetime T. The amplitude, A, is a pre-exponential factor that corresponds to f(o), the fluorescence intensity at time zero. The fluorescence lifetime is a characteristic of the molecules under observation. Under suitable conditions, the amplitude, A, is proportional to the concentration of the fluorescent molecules.

When the fluorescent system under observation consists of a heterogeneous population of emitting species, then, in principle, the impulse response takes the form of a sum of exponentials:

$$f(t) = \sum_j A_j \exp(-k_j t) \quad (2)$$

where the $k_j$ are the rate constants for emission by each species and $A_j$ correspond to the relative concentrations of each species.

There are cases where fluorescence decay curves can take a form other than those represented by Equations 1 and 2.

In practice, it is not possible to generate "instantaneous" excitation light pulses. Instead, light pulses of short duration relative to the decay being observed are employed. Since fluorescent lifetimes typically are in the range of nanoseconds, light pulses of a nanosecond, or less, duration are generally required. The finite duration of these exciting pulses distorts the measured impulse response of the system with the result that f(t) is no longer directly observable. Instead, one obtains the distorted response F(t) given by:

$$F(t) = \int_0^t E(t - t')f(t')dt' \quad (3)$$

where E(t) is the time profile of the exciting light pulse as measured by the detection system and t' is a point in time prior to t. In practice, therefore, the true impulse response f(t) is obtained from the measured E(t) and F(t) by mathematical deconvolution of Equation 3 (using a computer).

The above discussion presents the basic principles behind the technique of pulse fluorometry. The fluorescence decay curves F(t) obtained with this method provide useful information in the study of a wide variety of physical, chemical, and biological phenomena, and therefore, pulse fluorometry has become a well-established analytical tool.

In general, a pulse fluorometer consists of a pulsed light source for excitation of the sample; photodetector(s) for detecting the resultant fluorescence photons and generating an electrical signal; a signal processor for processing the information contained in the electrical signal; and a computer for data analysis. Within this general framework, a number of different methods and specific instrument configurations have been employed.

The fluorescence detection methods in common use fall into four categories: analog methods using a photomultiplier tube (PMT) and an oscilloscope; transient digitizers; time-correlated photon counting methods employing a time-to-amplitude converter (TAC) and a multichannel analyzer (MCA); and streak camera detection. Each of these approaches is briefly discussed below:

1. Analog Methods

In analog systems, the fluorescence emission is detected with a photomultiplier tube (PMT). The time-dependence of the emission is obtained by displaying the photocurrent output of the PMT on a cathode ray tube (CRT) oscilloscope. The time resolution of this approach is limited by the analog response time of the PMT and by the bandwidth of the CRT oscilloscope. The data, being in analog form, are not amenable to numerical computer analysis for deconvolution. This approach, therefore, is not suitable for analyses that require high precision and accuracy, such as when the decay is short relative to the width of the exciting pulse, or when multiexponential analysis, i.e., analysis of heterogeneous emissions is required. An additional drawback is that continuous irradiation of the sample with light pulses at a high repetition rate is necessary to obtain a relatively steady display of the fluorescence waveform.

Pulse sampling is another method that has been used for obtaining fluorescence decay curves. Specific devices that have been used for this purpose include the "box-car integrator" (Badea and Georghiou, *Rev. Sci. Instr.*, Vol. 47, 1976) and sampling oscilloscopes. In essence, with pulse sampling, the intensity of the fluorescence emission (output from the PMT) is sampled at a series of sequential time intervals which are delayed with respect to an excitation trigger. Only one point per waveform is sampled, therefore, the fluorescence decay is reconstructed, indirectly, from sampling a large number of events. With these methods, it is also necessary to irradiate the sample, repetitively, at a high rate. As one illuminates a fluorescent material repeatedly, the fluorescence characteristics may change due to bleaching or other photophysical effects. Useful fluorescence probes are often photolabile and degrade upon prolonged exposure to light.

2. Transient Digitizers

A different approach is that of devices that sample many points on the same waveform (see, for example, Crosby and MacAdam, *Rev. Sci. Instr.*, Vol. 52, 1981). Some of these devices perform an analog average over repeated signals for every sampled point. Digital instruments of this kind, known as transient digitizers, are also available. Devices of this type result in faster data acquisition, as compared to "single-point-perwaveform" apparatus. Conventional transient digitizers, based on fast analog-to-digital converters, are limited in resolution to about one point for every 2 nanoseconds and, thus, are not suitable to measure short-lifetime decays, nor can they be used for accurate multiexponential analysis in the nanosecond time scale.

3. Time-correlated Single Photon Counting Method

This is a method that circumvents the analog response of the PMT. Instead, the PMT is used to count and time the arrival of individual photons. The occurrence of the exciting light pulse starts a fast clock; detection of the first single photon at the PMT stops the clock. The duration of the time interval elapsed between start and stop is stored. The cycle is repeated a large number of times until a histogram of the distribution of the time intervals measured can be constructed with the desired precision. This histogram then represents the time-dependence of the fluorescence decay.

In practice, the fast clock takes the form of a device called a time-to-amplitude converter, and the data are stored in a multichannel analyzer (for further details, see the Fernandez reference, cited above, or "Time Decay Fluorometry by Photon Counting" by I. Isenberg in *Biochemical Fluorescence*, Chen & Edelhoch (Eds.), Marcel Dekker, 1975). In order that the histogram of time intervals, obtained by this method, be an accurate representation of the fluorescence decay, statistical considerations dictate that the probability of more than one photon arriving at the detector during each measurement cycle, be very small. This requires that the photon counting rate be not more than 1% of the light source repetition rate.

An advantage of this method is that the data is obtained in digital form and, thus, can be easily manipulated and analyzed by computer. A drawback is that the sample must be repetitively excited a large number of times before data of sufficient precision is acquired. This is a serious limitation when the nature of the application requires data of high precision but rapid collection time, or when the sample degrades upon prolonged exposure to exciting radiation. For example, with a lamp repetition rate of 10 KHz, the maximum allowed photon counting rate is of the order of 100 photons per second (1%). For a multiexponential decay curve consisting of 256 data points, a total of 10 million counts may be required to be collected to achieve sufficient precision. At the stated count rate, it would take approximately 28 hours to collect the data. Even if one million counts were sufficient, data collection would still be of the order of three hours.

There are certain applications of pulse fluorometry where it is necessary to collect several decay curves, from a sample, in a relatively short time. For example, in studies of the time-dependence of the fluorescence emission anisotropy, two decay curves of different polarization must be collected. This would double the data collection time. In studies of time-resolved emission spectra, it is necessary to collect a family of curves at different wavelengths. With the time-correlated single-photon counting approach, the data collection time may become unacceptably long, especially in the case of weakly emitting samples.

4. Streak Camera Detection

When the fluorescence pulse is very intense, a streak camera can be used to detect the decay (see, for example, "Topics" in *Applied Physics*, S. L. Shapiro, (Ed.), Vol. 18, Springer-Verlag, 1977). Generally, this method is useful when picosecond resolution is required. Streak cameras, however, are extremely expensive.

DISCLOSURE OF THE INVENTION

The present invention circumvents the need to repetitively excite a sample over a period of time and is capable of generating digital data of high precision in an extremely short time, i.e., less than one second per sample. The cost of the apparatus, which is assembled from commercially available components, is low, compared to alternative approaches.

The apparatus comprises a stable pulsed laser light source for emitting substantially monochromatic light to excite fluorescence in a sample contained in a sample holder. Optical filter elements are employed to isolate a narrow optical band of the emitted fluorescence from the sample. A photomultiplier tube (PMT), optimized for linearity and response time, is used to detect the fluorescence transient, i.e., the photons emitted over the decay time period produced by a single excitation pulse from the laser. The PMT produces photoelectrons at the PMT photocathode in response to the fluorescence photons. The photoelectrons are accelerated through a series of dynodes in a vacuum to generate cascades of secondary electrons. These secondary electrons form a small current pulse at the PMT anode. This current pulse is discharged through a resistance/capacitive (RC) network to produce a time varying voltage amplitude signal. This electrical voltage waveform is then converted to an optical image, intensified and stored for digitization. Conversion to an optical waveform may be conveniently accomplished by coupling the PMT voltage signal to the vertical sweep of a CRT while driving the horizontal input with a fast sweep generator; thereby displaying the voltage amplitude signal on the CRT face. The waveform image on the CRT is intensified by a microchannel plate (MCP) image intensifier. The image intensifier is optically coupled to a solid state image sensor, such as a charge coupled device (CCD), which stores the image. This stored image is decoded into a digitized data set by known means and sent to buffer memory.

The response E(t) of the detector system to the laser pulse is also detected and digitized and stored in memory, as above. The buffered digitized waveforms are then processed, as follows, in a computer to determine the true fluorescence impulse response. The true fluorescence impulse response f(t) to a single excitation pulse has been masked, or distorted, by the finite width of the exciting pulse and by the impulse response o the detector circuit. Thus, the signal stored in memory is not the true fluorescence impulse response f(t), but a distorted version thereof, F(t). The computer, by an iterative data fitting process determines the parameters of the true fluorescence impulse response f(t), by convoluting E(t) with a trial function corresponding to an estimate of f(t). The trial function is chosen on the basis of physico-chemical considerations. Parameters of the trial function are adjusted to generate a calculated function $F(t)_{calc}$, which is compared point-by-point with the actually measured fluorescent decay curve F(t).

The variance between the two curves, i.e., the measured versus the calculated curve, is minimized by a "least square" method, to obtain parameters that best fit the experimental data. To do this, the parameters of the trial function curve are adjusted, iteratively, until the "chi-square" function "$\chi^2$", that describes the variance between the experimentally measured fluorescent decay curve and the calculated decay curve, is minimized. At each iteration step, the minimization criteria lead to improved values of the parameters until successive values of the chi-square function differ by less than some arbitrarily chosen convergence criteria.

Unlike the prior art time-correlated single photon counting technique, the method of the present invention processes substantially all the photons excited by a single excitation pulse arriving at the photomultiplier. Furthermore, fluorescence decay curves of sufficient accuracy to perform multiexponential analysis by deconvolution are collected from one single excitation pulse. Thus, it is not necessary to repetitively excite the sample. These and other features and advantages of the invention will now be described in detail in connection with the following drawings.

BEST MODE OF CARRYING OUT THE INVENTION

Figure 1:
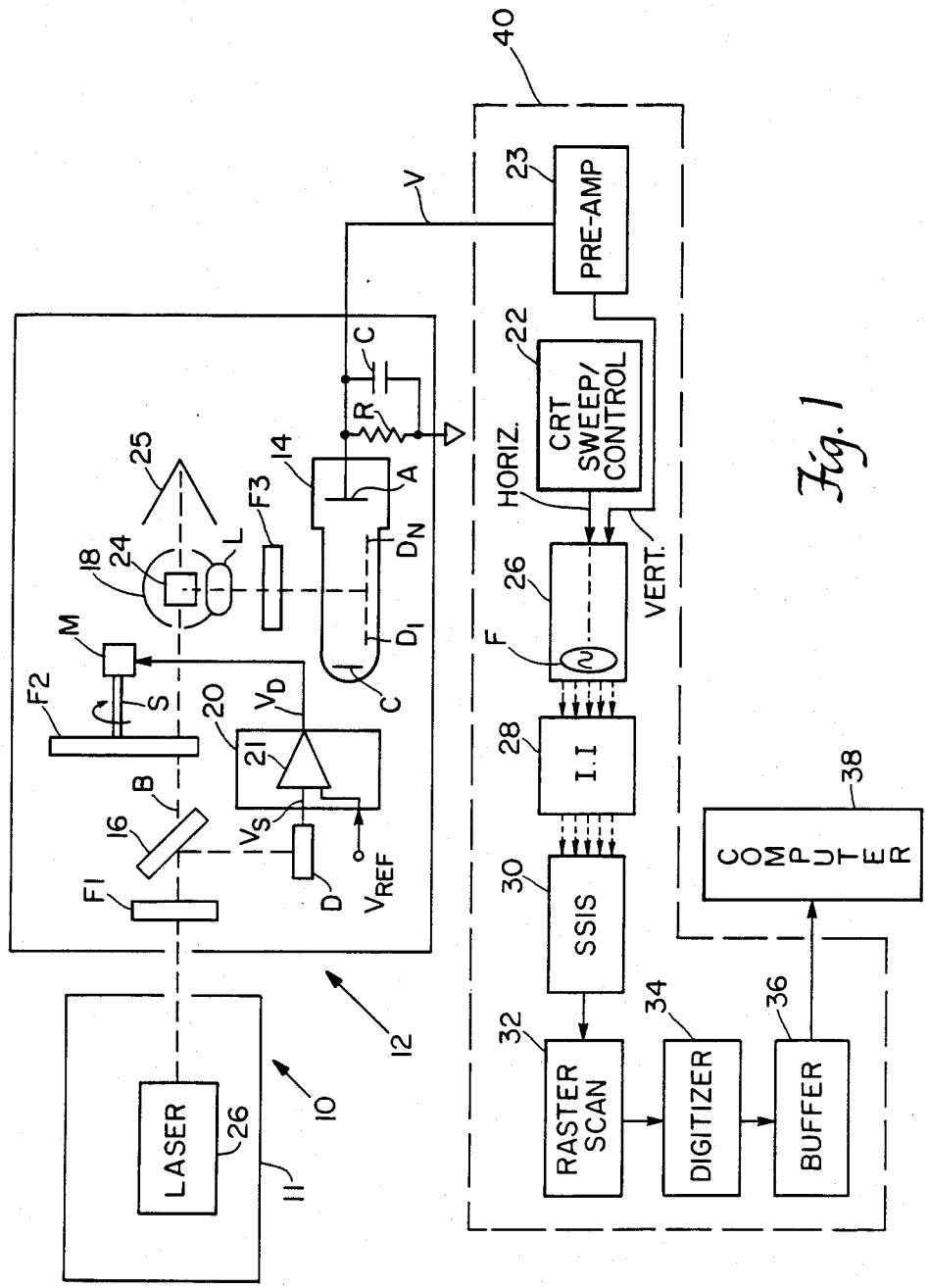
FIG. 1 is a block diagram of a time resolved fluorometer, in accordance with the invention.

Generally, the apparatus of the invention consists of a laser module 10, a sample compartment 12, an image/storage/digitizer system 40, and a computer 38. Within the laser module, a pulsed laser 26, preferably a nitrogen dye laser, is contained in an RFI/EMI shielded compartment 11 electrically isolated from sample compartment 12. Suitable power supply and control logic circuitry is also enclosed, but not shown, within module 10. A single excitation pulse (dotted line) from laser 26 is used to excite a sample 24 disposed on, or within, a holder 18 in compartment 12. Preferably, laser 26 provides an energy output of at least 15 microjoules per pulse. This is equivalent to approximately $3 \times 10^{13}$ photons per pulse. The full width at half-maximum of each pulse is preferably about 3, or less, nanoseconds. This pulse energy should be substantially stable and repeatable over long periods of time. The spectral bandwidth of the laser pulse is preferably less than 1 nanometers, so that the light is essentially monochromatic. With a $N_2$/DYE laser output wavelengths are tunable within a range of 360–900 nanometers.

The sample 24 may be in liquid form and contained in a quartz cuvette of conventional design. Alternatively, the sample may be in solid form and held in a suitable sample holder. The laser pulse is passed through a neutral density filter $F_1$ and impinges on a beam splitter, or beam sampler, 16. About 10% of the light is reflected to a reference diode detector D. The other 90% passes through a rotatable graduated neutral density filter $F_2$ to the sample 24 to produce fluorescence photons which are focused by lens L, passed through a narrow passband interference filter $F_3$ and impinge on the sensitive area of PMT 14, producing photoelectrons at the cathode C thereof. These electrons are accelerated by successive dynode stages $D_1$–$D_N$ producing secondary electrons and, ultimately, a small current at anode A. This current is passed through R/C load circuit to ground producing a voltage amplitude waveform V, which is coupled via a preamplifier 23 to the vertical input, Vert, of the CRT 26. The horizontal input, Hor'z, of the CRT is coupled to a fast sweep generator 22. In this manner, substantially all the fluorescent light photons reaching the PMT 14 from the excited sample are converted to photoelectrons to produce the amplitude varying voltage waveform V displayed on the face F of CRT 26.

The portion of the laser light split at beam sampler 16, is detected by diode detector D, and is used, via filter control circuit, 20, to control the rotational position of a gradient density filter $F_2$ disposed in the main path of the photon beam B. Filter $F_2$ is mounted on a rotatable shaft S coupled to motor M. Motor M is controlled by a well-known servomechanism comprising a difference amplifier 21 having two input signals $V_S$ and $V_{REF}$. $V_S$ is the voltage signal sensed by detector D and $V_{REF}$ is a fixed voltage reference level. The output of amplifier 21 is a difference or error voltage $V_D$. Thus, by providing an error signal $V_D$, a suitable sensor control signal from circuit 20 can be generated to control the position of motor M to maintain a constant incident light intensity or to attenuate it appropriately, i.e., to prevent photodetector saturation.

Beam stopper 25 is a light trap, which is used to prevent undesirable back scatter by absorbing specular reflection. Filter $F_3$ is a narrow bandpass interference filter which minimizes the effects of Raman scattering, which often occurs at wavelengths between that of the exciting beam and those of the fluorescent emissions.

It is important, from the standpoint of instrument sensitivity, that substantially all the photons reaching the PMT detector surface from a single excitation pulse contribute to the useful output voltage signal. This means that these photons must be detected and converted to photoelectrons and collected at the anode in about ½ microsecond or less. Therefore, the PMT should be optimized for speed, range and linearity rather than gain as is customary in other applications.

The analog time variant voltage amplitude signal corresponding to the fluorescence decay curve of the excited sample is displayed on the face F of CRT 26 for a time period that depends upon the persistence of the materials used on the CRT face. Because of the high sweep rate, the CRT trace is of low intensity and the waveform must be intensified and stored so that it can be digitized via scanning analog to digital (A/D) circuitry. This is accomplished via a microchannel plate image intensifier 28, optically coupled to CRT face F, and employed to intensify the CRT display image. The intensified image is then optically coupled to a solid state image sensor 30, a charged coupled device (CCD) which stores the image in the form of charges of varying magnitude on an array of CCD's. The stored image is then raster scanned by a raster scan circuit 32, digitized in digitizer 34 and stored in frame buffer 36 for analysis by computer 38. The impulse response of the system to the exciting laser pulse is also processed, as above, and stored in memory by replacing the sample 24 with a non-fluorescent light scattering material, such as latex microspheres.

The digitized data transmitted to the computer 38 from the buffer 36 consists of sets of numbers which represents points on a plot of the variation of the intensity versus time of the excitation light pulse and of the emitted fluorescence respectively. As previously noted, the intensity-time profile thus obtained is not an accurate representation of the true time profile of the fluorescence emitted. Distortions, due to the instrument response characteristics, affect the time profiles measured. These distortions can be grouped into two types: Those arising from the time response of the photomultiplier tube (PMT) 14 and associated circuitry and those arising from the finite duration of the excitation light pulse from the laser.

A. Distortions Arising from the Finite Width of the Exciting Pulse

The laser pulse used to excite the fluorescent sample is not a true impulse function, since its time profile e(t) has a finite width. Consequently, different molecules of the fluorescent sample are excited and begin emitting light at different times. This produces a distortion, which is most significant at the beginning of the fluorescence decay and with fluorophores having a short decay time. In any case, it complicates the process of establishing the origin of the waveform, which must be accomplished accurately if subsequently determined concentration values are to be valid. The time profile F'(t) of the fluorescence emission, as distorted by the finite duration of the incident exciting pulse, is given by the convolution integral of the exciting pulse shape e(t) and the true fluorescence impulse response function f(t):

$$F(t) = \int_0^t e(t')f(t - t')dt' \quad (4)$$

Wherein, F'(t) represents the time profile of the fluorescence signal incident on the photomultiplier, and f(t) is the waveform of interest and t' is a point in time prior to t.

B. Distortions Arising from the PMT and Associated Circuitry

The response of the PMT 14 and its associated circuitry is neither instantaneous nor linear over the full dynamic range. Thus, the PMT response to a time-varying incident light signal is not an exact representation of the incident time profile, but is distorted by the PMT characteristics. This fact alters the shape (time profile) of the observed data curves of both the excitation pulse e(t) and the fluorescence decay f(t) curves.

As previously stated, the detector is first set up to directly observe the exciting pulse by replacing the fluorescent sample, 24, in the sample holder 24a with a non-fluorescent scatterer and allowing the scattered incident light to reach the PMT 14. The output of the PMT will not, in practice, be an accurate representation of the incident pulse time-profile, due to the PMT impulse response characteristics. If the true time profile of the exciting light pulse is designated e(t), then the measured time profile will be a distorted function E(t). E(t) is related to e(t) by a convolution similar to that of Equation 1. Namely, E(t) is the convolution integral of the true light pulse shape e(t) and the impulse response of the PMT and its associated circuitry, I(t):

$$E(t) = \int_0^t I(t')e(t - t')dt' \quad (5)$$

When a fluorescence decay curve is to be observed, the appropriate fluorescent sample 24 is placed in the sample holder 18, and a suitable narrow bandpass optical filter $F_3$ is placed in front of the PMT to isolate the spectral range of the fluorescence and to reject scattered incident light. As discussed above, the time profile of the fluorescence signal incident on the PMT is F'(t) and is given by Equation 4. This signal F'(t) will also be distorted by the impulse response of the PMT and associated circuitry, so that the output of the PMT will be a distorted function F(t), where the incident signal F'(t), and the observed signal F(t) are related through a convolution integral with the PMT impulse response I(t), similar to Equation 5:

$$F(t) = \int_0^t I(t')F(t - t')dt' \quad (6)$$

C. The True Fluorescence Impulse Response

As shown above, the experimentally determined waveforms E(t) and F(t) are distorted versions of the true exciting light pulse profile e(t) and the fluorescence signal incident on the PMT, F'(t). Furthermore, E(t) represents the light pulse distorted by the detector impulse response, and F(t) is a representation of the true fluorescence impulse response f(t) that has been distorted twice. The first distortion is caused by the finite width of the exciting pulse (Equation 4) and the second, by the impulse response of the detector I(t).

The waveform of interest is f(t), the true fluorescence impulse response, and it is not directly observable. It can be shown that f(t) is related to the experimentally determined waveforms E(t) and F(t) by the following convolution integral:

$$F(t) = \int_0^t E(t')f(t - t')dt' \quad (7)$$

The waveform f(t) can be obtained from Equation 7 by computer analysis, as described below in connection with the flow chart of FIG. 2.

D. Computer Analysis

Two sets of data are obtained, as above. One set represents E(t), the amplitude versus time waveform, or curve, of the observed exciting light pulse, and the other represents F(t), the observed fluorescence decay curve. From these two sets of data, f(t) is calculated by computer analysis from Equation 7. E(t) and F(t) are described by sets of N numbers which are stored in the computer for numerical analysis. Each member of the number sets represents the digitized value of a point on one of the curves. These values are read and, decoded from the data stored in frame buffer 36 (See Step 1, FIG. 2). N such data points for each curve are selected to represent each of the waveforms E(t) and F(t) (See Step 2, FIG. 2). Typically, 100 data points (N=100) are sufficient to represent each curve with the desired degree of precision.

The definition of the nomenclature employed for the various waveforms is repeated below:

e(t) = true shape of the exciting light pulse as emitted by the laser

E(t) = observed shape of the exciting light pulse as distorted by detector f(t) = true fluorescence impulse response function F'(t) = fluorescent signal incident on the PMT distorted by shape of exciting light pulse F(t) = observed fluorescent signal distorted by both the light pulse and the detector In order to obtain the parameters that best characterize f(t), an analytical expression for f(t) is assumed a priori. This analytical expression is called the "trial function", and is based on the physical nature of the problem. For example, in the case of a single non-reactive fluorescent species, it is known by physico-chemical considerations that the fluorescence decay is essentially exponential in nature, therefore, a trial function which is a single exponential decay, is chosen for this case (See step 3 FIG. 2), i.e.:

$$f(t) = A\exp(-t/T) \quad (8)$$

In this example, the two parameters, A and T, fully characterize f(t). A is the amplitude of the fluorescence waveform, and T is the fluorescence lifetime. The determination of these two parameters is the ultimate goal of the measurement process.

If the sample contains two non-reacting fluorescent species, then physico-chemical considerations dictate that the trial function be a sum of two exponentials, i.e.:

$$f(t) = A_1\exp(-t/T_1) + A_2\exp(-t/T_2) \quad (9)$$

where now four parameters, two amplitudes, A1 and A2, and two lifetimes, T1 and T2, are necessary to fully characterize the fluorescence decay f(t) of the two species.

Once a trial function is chosen on the basis of physico-chemical considerations, such as known fluorescence decay kinetics, the parameters that best characterize it, based on the measured E(t) and F(t) must be found. These parameters, once determined, constitute the "result" of the measurement. Therefore, in the next step (Step 4, FIG. 2), a set of trial parameter values for the trial function are chosen; again, based on prior experience as to anticipated ranges of values.

Figure 2:
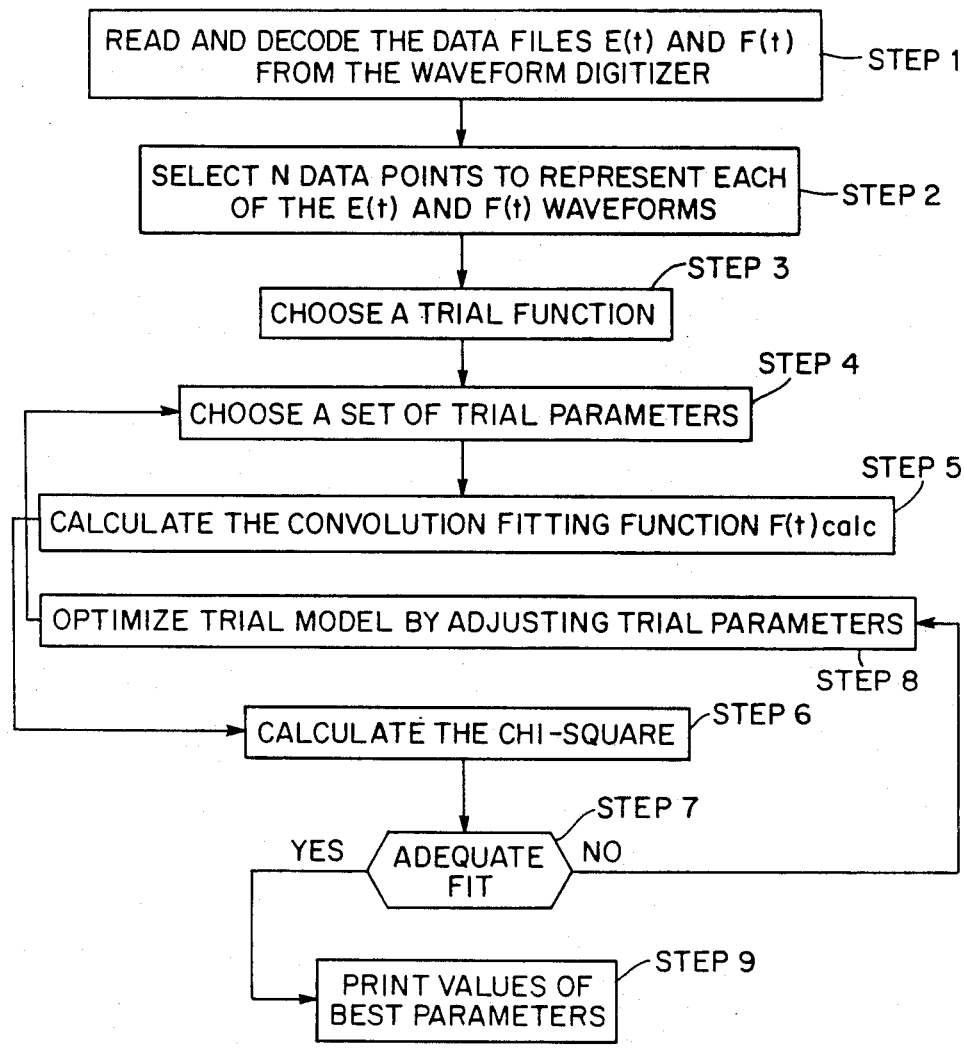
FIG. 2 is a flow chart of the process for determining parameters of the digitized waveforms.

Determination of the best parameters is accomplished by an iterative data fitting process, whereby the trial function, with adjustable trial parameters, e.g., A and T, is convoluted with E(t) to generate a calculated F(t), according to Equation 7 (Step 5, FIG. 2). Let this calculated version of F(t) be called trail function F(t)$_{calc}$ and, hence, as A and T are changed F(t)calc changes. Now trail function F(t)$_{calc}$ is compared point-by-point with the measured F(t) to calculate the variance between the two curves (Step 6, FIG. 2).

A least squares method (see, for example, "Least Squares Method of Analysis", B. K. Selinger, et al., in *Time Resolved Fluorescence Spectroscopy in Biochemistry and Biology*, R. B. Cundall and R. E. Dale, Eds., Plenum Press, New York, 1983) is used to obtain the parameters that best fit the experimental data. In essence, this is accomplished by selecting a new "best guess" trial function if an adequate fit between the first trial function and the experimental data is not achieved (Step 7, FIG. 2). The "best guess" trial function is optimized by adjusting its parameters iteratively (Step 8, FIG. 2), until the chi-square function, $\chi^2$ that describes the variance between F(t) and trail function F(t)$_{calc}$ is minimized. The chi-square function is given by:

$$\chi^2 = \frac{1}{N-1} \sum_{I=1}^{N} \frac{[F(I) - F_{calc}(I)]^2}{F(I)} \quad (10)$$

wherein:

N = the number of data points

I = an integral index number which identifies the data points and ranges from I=1 to N

|F(I)| = the absolute magnitude of F at point I

The process of searching for the best parameters is optimized by simultaneously varying the set of fitting parameters according to the algorithm of Marquardt (Marquardt, D. W., 1963, "An Algorithm for Least-Squares Estimation of Non-Linear Parameters", *J. Soc. Industr. Appl. Math.*, 11, 431-441). At each iteration step, the minimization criteria lead to improved values of the parameters until successive values of the chi-square function differ by less than some arbitrarily chosen convergence criterion. Once an adequate fit is obtained i.e. successive values of the chi-square function differ by less than the chosen convergence criterion, the YES path of Step 7, FIG. 2 is followed and the values of the best parameters are printed, (Step 9, FIG. 2).

In the event the successive chi-square function values differ by more than the chosen criterion; the NO path of Step 7, FIG. 2 is followed and the trial model is optimized by adjusting trial parameters, (Step 8, FIG. 2).

Figure 3:
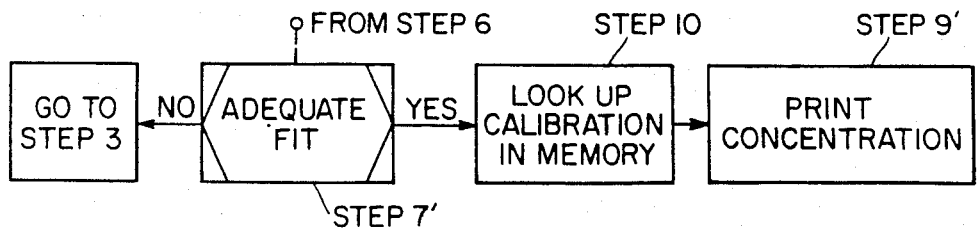
FIG. 3 is a flow chart of the steps for obtaining the concentration parameter of a fluorescent sample of known T.

Alternatively, as shown in FIG. 3, the "adequate fit" parameters from Step 6, FIG. 2, may be compared with calbiration points form a calibration curve stored in memory (The YES path to Step 10, FIG. 3). The curve may be obtained in advance by analyzing a series of samples of known concentration and generating a look up calibration table of the amplitude parameter A versus actual concentration. Based on this comparison, the actual concentration may be printed (Step 9' FIG. 3).

E. Application to Time-Resolved Immunoassay

In the preceding description, the problem of data handling and the analysis of fluorescent decay spectra, was described generally, without reference to any specific application. Specific examples of the use of the method and apparatus of the invention for the performance of a fluorescent immunoassay is now described in connection with FIG. 3.

The immunoassays are described in U. S. Patent Application entitled: "Time Resolved Fluorescence Immunoassay", now U.S. patent application Ser. No. 07/031,408 filed Mar. 27, 1987.

In this example, the fluorescence from an immunoassay sample is analyzed. In the simplest form, such a sample may comprise a fluorescent species, namely, a fluorescently labelled probe employed in the immunoassay.

For example, in a standard competitive type immunoassay, an analyte competes with a fixed amount of fluorescently labelled analyte (probe) for binding to antibody against the analyte. The concentration of labelled analyte bound to the antibody is indirectly proportional to the amount of analyte present in a test sample. In a noncompetitive type immunoassay, a fluorescently labelled antibody is used as a probe for analyte complexed with a first (capture) antibody (present in excess) against the analyte. The label associated with the complex is directly proportional to the amount of analyte in a sample.

From physico-chemical considerations, the fluorescence decay curve f(t), for the fluorescent label, is represented by a single exponential:

$$f(t) = A\exp(-t/T) \tag{11}$$

The lifetime T is known a priori, since a well-characterized probe of known fluorescent lifetime is chosen as the fluorescent label for the reagent (e.g., labelled analyte or labelled antibody, depending on the format of the immunoassay). The amplitude A is the only unknown and is the parameter sought by the analysis. A is proportional to the concentration of the fluorescent species (labelled analyte or labelled antibody), and, therefore, to the concentration of analyte.

To perform the analysis in this example, a trial function of the form of Equation 11 is chosen in Step 3, FIG. 2, and the known lifetime parameter T of the probe is also fixed to its known value in Step 4, FIG. 2. The function of the next steps in the analysis is simply to find the best value of A.

The value of A, thus obtained, is proportional to the concentration of the analyte. In order to determine the absolute concentration of the analyte from A, the value of A is compared to a calibration curve which has been previously obtained and stored in the memory of computer 38. In other words, prior to analyzing the unknown sample, a series of standard samples of known concentration are analyzed, so that a calibration table can be made of values of A versus concentration.

This addition step (Step 10) is shown in the FIG. 3 flow chart of the computer program.

The procedure for a double analyte immunoassay is similar. In a competitive type assay, a fixed amount of each of two labelled analytes is employed with antibody against each analyte. In the noncompetitive format two different capture antibodies, each specific for one of the analytes, are used and two fluorescently labelled antibody probes, each having different fluorescence lifetimes, are used to determine the amount of each analyte-capture antibody complex. In this case, the trial function is a sum of two exponentials:

$$f(t) = A_1\exp(-t/T_2) + A_2\exp(-t/T_2) \tag{12}$$

The two lifetimes, $T_1$ and $T_2$, are known and the computer fits the two amplitudes, A1 and A2, that are proportional to the concentrations of each analyte. The calibration curve for the computer memory and comparison Step 10, is generated from a series of standard solutions which contain both analytes in appropriate known concentrations.

Equivalents

This completes the description of the preferred embodiments of the invention. Modifications may be made without departing from the scope of the invention, which should not be limited, except as provided in the following claims. For example, while the invention has been described in terms of time varying voltage amplitude signals produced by a PMT detector, other optical detectors, such as photodiodes and multichannel plate devices, may be substituted therefore. Also, rather than displaying the voltage varying waveform from the photodetector as a two-dimensional image on a CRT, the output of the photodetector can be used to modulate the intensity of the electron beam in the CRT to encode the waveform into a one-dimensional linear array detector.

We claim:

1. A method for fluorescent spectroscopy of material, comprising the steps of:
   (a) exciting the material with a single pulse of light energy to induce fluorescence;
   (b) detecting in a detector a signal corresponding to the fluorescence transient waveform induced by said single pulse, as distorted by said detector and said pulse, and generating an electrical signal F(t) corresponding to said distorted signal;
   (c) detecting in said detector a signal, which corresponds to said single pulse, as distorted by the impulse response of said detector, and generating an electrical signal E(t);
   (d) separately displaying an image of said waveforms F(t) and E(t);
   (e) digitizing a predetermined number of data points on each such image, as digital numbers representing points on said waveforms;
   (f) storing said numbers in memory as data points of E(t) and F(t); and
   (g) calculating the true fluorescence impulse response waveform f(t) from the stored data point numbers.

2. The method of claim 1 wherein the images displayed in step (d) are intensified and then stored in an image storage device for subsequent digitizing.

3. The method of claim 2 wherein the detector comprises a photomultiplier tube and the waveforms are in the form of amplitude varying voltages provided at the output of the photomultiplier tube.

4. The method of claim 3 wherein the voltage is applied to a sweep circuit of a cathode ray tube for display as an image on the face thereof and said image is intensified and stored by a charge-coupled device.

5. The method of claim 1 wherein the true fluorescence impulse waveform is calculated by convoluting E(t) with a predetermined trial function f (t) having adjustable parameters and comparing the data points of the resulting convoluted $F(t)_{calc}$ with data points corresponding to F(t) data points.

6. The method of claim 5 wherein the predetermined trial function curve $F(t)_{calc}$ is determined by physicochemical considerations of the known characteristics of the constituents in the material.

7. The method of claim 5 wherein the material comprises a plural number i of fluorescent species and the trial function is the sum of a plural number i, of exponential curves $A_1\exp(-t/T_1) + A_2\exp(-t/T_2)$ --- $A_i\exp(-t/T_i)$.

8. The method of claim 5 wherein the parameters of the trial function curve $F(t)_{calc}$ are iteratively adjusted until a best fit is achieved between the trial function curve $F(t)_{calc}$ and the stored curve F(t).

9. The method of claim 8 wherein a best fit occurs when the variance between $F(t)_{calc}$ and F(t) is minimized when successive values of the chi-square function thereof differ by less than a predetermined amount.

10. The method of claim 5 wherein the material comprises a single fluorescent species, the trial function curve is an exponential curve in the form of $A\exp(-t/T)$ wherein the parameter A is the amplitude and T is the fluorescent decay lifetime.

11. The method of claim 10 wherein the material is tagged with a know fluorescent specie and T is therefore known in advance and the parameter A is proportional to the concentration of the fluorescent species in the material.

12. The method of claim 10 wherein the material is tagged with at least two known fluorescent specie having known fluorescent decay lifetimes which are known in advance and the amplitude parameter is proportional to the concentration of each fluorescent specie in the material.

13. The method of claims 11 or 12 wherein the absolute concentration of the fluorescent specie is determined by comparing the calculated amplitude parameter with a curve stored in computer memory; said curve having been obtained in advance by analyzing a series of samples of know concentration and generating a table of the amplitude parameter A versus actual concentration.

14. Apparatus for fluorescent spectroscopy of material, comprising:
  (a) a stable source of light pulses for exciting the material with a single pulse of light energy to induce fluorescence;
  (b) detector means for separately:
    (i) detecting the fluorescence transient waveform induced by said single pulse, as distorted by said detector means and generating an electrical waveform signal F(t) corresponding thereto, and
    (ii) detecting the waveform, which represent said single pulse, as distorted by the impulse response of said detector means and generating an electrical waveform signal E(t) corresponding thereto,
  (c) image display means responsive to said electrical signals for separately displaying an image of said waveform signals F(t) and E(t);
  (d) digitizing means for producing a predetermined number of data points on each such image, as digital numbers representing points on said waveform signals;
  (e) storage means for storing said numbers in memory as data points of E(t) and F(t); and
  (f) computer means for calculating the true fluorescence impulse response waveform f(t) from the stored data points.

15. The apparatus of claim 14 wherein the light source comprises a pulsed laser, the detector means comprises a photomultiplier tube for generating output electrical signals, the electrical signals are voltage amplitude waveforms, the image display means comprises a cathode ray tube having an input sweep circuit, which sweep circuit is coupled to the output electrical signals from said photomultiplier tube for displaying said voltage waveforms on the face of the cathode ray tube, and image intensifier means for intensifying the image on said face and an image storage device coupled to said intensifier means for storing said image as charges on an array of charge-coupled devices.

16. The apparatus of claim 14 including beam splitter means for sampling a portion of the light energy to generate control signal to maintain a constant light intensity input to the detector means.

17. The apparatus of claim 16 wherein the detector means comprises a photomultiplier tube, the light pulses comprise pulses of laser energy which induce fluorescence photons, said light energy is split by said beam splitter into a main beam and a sampling beam, said sampling beam is detected to generate a control signal which is used to control the position of a gradient density filter in the path of the main beam to maintain constant light intensity to the input of said photomultiplier tube.

18. The apparatus of claim 14 including means for calculating the true impulse response function convoluting E(t) with a predetermined trial function t(f) having adjustable parameters and comparing the data points of the convoluted $F(t)_{calc}$ with data points corresponding to the F(t) data points.

19. The apparatus of claim 18 including means for adjusting the parameters of the trial function curve $F(t)_{calc}$ until a best fit is achieved between the trial function curve $F(t)_{calc}$ and the stored curve F(t).

20. The apparatus of claim 18 wherein the material comprises a plural number i of fluorescent species and the trial function is the sum of a plural number, i, of exponential curves $A_1\exp(-t/T_1)+A_2\exp(-t/T_2)$ --- $A_i\exp(-t/T_i)$.

21. The apparatus of claim 18 wherein the material is tagged with at least two known fluorescent specie having known fluorescent decay lifetimes which are known in advance and the amplitude parameter is proportional to the concentration of each fluorescent specie in the material.

22. The apparatus of claim 18 wherein the material comprises a single fluorescent species, the trial function curve is an exponential curve in the form of $A\exp(-t/T)$ wherein the parameter A is the amplitude and T is the fluorescent decay lifetime.

23. The apparatus of claim 22 wherein the material is tagged with a known flurescent specie and T is therefore known in advance and the parameter A is proportional to the concentration of the fluorescent species in the material.

* * * * *